United States Patent
Fukuda et al.

(10) Patent No.: US 9,901,662 B2
(45) Date of Patent: *Feb. 27, 2018

(54) ADHESION PREVENTING MATERIAL (71) Applicant: OTSUKA PHARMACEUTICAL FACTORY, INC., Naruto-shi, Tokushima (JP)

(72) Inventors: Tatsuru Fukuda, Naruto (JP); Hirofumi Tamura, Naruto (JP)

(73) Assignee: OTSUKA PHARMACEUTICAL FACTORY, INC., Naruto-shi, Tokushima (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/888,973

(22) PCT Filed: May 28, 2014

(86) PCT No.: PCT/JP2014/064123
§ 371 (c)(1),
(2) Date: Nov. 4, 2015

(87) PCT Pub. No.: WO2014/192807
PCT Pub. Date: Dec. 4, 2014

(65) Prior Publication Data
US 2016/0095962 A1    Apr. 7, 2016

(30) Foreign Application Priority Data

May 29, 2013 (JP) .................. 2013-113336

(51) Int. Cl.
A61L 31/04 (2006.01)
A61L 31/14 (2006.01)

(52) U.S. Cl.
CPC ........... A61L 31/041 (2013.01); A61L 31/042 (2013.01); A61L 31/145 (2013.01); *A61L 2400/06* (2013.01)

(58) Field of Classification Search
CPC .... A61L 31/041; A61L 31/145; A61L 31/042; A61L 2400/06; C08L 5/04
USPC ............................................. 514/54; 536/3
See application file for complete search history.

(56) References Cited

U.S. PATENT DOCUMENTS

| | | |
|---|---|---|
| 2005/0003010 A1 | 1/2005 | Cohen et al. |
| 2005/0137272 A1 | 6/2005 | Gaserod et al. |
| 2006/0052747 A1 | 3/2006 | Nishimura et al. |
| 2007/0060876 A1 | 3/2007 | Bassarab et al. |
| 2007/0254016 A1 | 11/2007 | Andersen et al. |
| 2009/0314803 A1 | 12/2009 | Keller |
| 2009/0317474 A1* | 12/2009 | Van Den Plas ...... A61K 31/765 424/487 |
| 2012/0165773 A1* | 6/2012 | Nakashita ............ A61F 13/532 604/364 |
| 2014/0308365 A1* | 10/2014 | Fukuda ................ A61K 31/734 424/602 |

FOREIGN PATENT DOCUMENTS

| | | |
|---|---|---|
| CN | 1829501 A | 9/2006 |
| JP | 04-364851 A | 12/1992 |
| JP | 2001-104482 A | 4/2001 |
| JP | 2003-153999 A | 5/2003 |
| JP | 2003-159328 A | 6/2003 |
| JP | 2005-006945 A | 1/2005 |
| JP | 2006-525405 A | 11/2006 |
| JP | 2007-505183 A | 3/2007 |
| JP | 2009-504523 A | 2/2009 |
| JP | 2009-529926 A | 8/2009 |
| JP | 2010-501420 A | 1/2010 |
| WO | 2004105737 A2 | 12/2004 |
| WO | 2013/077414 A1 | 5/2013 |

OTHER PUBLICATIONS

Se Heang Oh et al., "Prevention of postsurgical tissue adhesion by anti-inflammatory drug-loaded pluronic mixtures with sol-gel transition behavior", Journal of Biomedical Materials Research Part A, 2005, pp. 306-316, vol. 72, No. 3.
A.A. Chaturvedi et al., "Prevention of postsurgical adhesions using an ultrapure alginate-based gel", British Journal of Surgery, Apr. 17, 2013, internet:<URL: http://onlinelibrary.wiley.com/doi/10.1002/bjs.9131/abstract>.
Kozo Shimada et al., "Development of Alginic Acid Solution for Inhibition of Posttraumatic Peritendinous Adhesion : Validation for Physical Property of Alginic Acid Solution", The Journal of Japanese Society for Surgery of the Hand, 2002, p. S77, vol. 19, No. 1.
Catherine K. Kuo et al., "Ionically crosslinked alginate hydrogels as scaffolds for tissue engineering: part 1. Structure, gelation rate and mechanical properties", Biomaterials, 2001, pp. 511-521, vol. 22, No. 6.
International Search Report for PCT/JP2014/064123 dated Aug. 19, 2014.
Communication dated Jan. 2, 2017, from the European Patent Office in counterpart European Application No. 14803605.6.
Communication dated Mar. 3, 2017, issued by the State Intellectual Property Office of P.R.C. in corresponding Chinese Application No. 201480030318.2.

* cited by examiner

Primary Examiner — Shaojia A Jiang
Assistant Examiner — Yih-Horng Shiao
(74) Attorney, Agent, or Firm — Sughrue Mion, PLLC (57) ABSTRACT

An object of the present invention to provide an antiadhesive material designed to have time-varying fluidity as it exhibits a gel form of high fluidity at the time of administration, and exhibits a gel form of low fluidity after it is administered to an incised and sutured site. A powdery antiadhesive material to be mixed with an aqueous solvent upon use containing alginic acid and/or a salt thereof, that is configured to be mixed with the aqueous solvent upon use so that the viscosity at 37° C. is less than or equal to 70 mPas·s at the time of 5 minutes after mixing with the aqueous solvent, and the viscosity at 37° C. is more than or equal to 120 mPas·s at the time of 60 minutes after mixing, will have high fluidity at the time of administration when it is mixed with an aqueous solvent upon use in a clinical scene, and have low fluidity after it is administered to an incised and sutured site, and thus is capable of satisfying both the excellent operability and the antiadhesive effect.

7 Claims, 5 Drawing Sheets

ADHESION PREVENTING MATERIAL

CROSS REFERENCE TO RELATED APPLICATIONS

This application is a National Stage of International Application No. PCT/JP2014/064123 filed May 28, 2014, claiming priority based on Japanese Patent Application No. 2013-113336 filed May 29, 2013, the contents of all of which are incorporated herein by reference in their entirety.

BACKGROUND OF THE INVENTION (1) Field of the Invention

The present invention relates to a powdery antiadhesive material to be mixed with water upon use, having excellent operability in medical scenes, and an excellent antiadhesive effect with biological tissues.

(2) Description of Related Art

Adhesion refers to a condition that continuity arises between the organs or the tissues that are originally located close to each other but liberated from each other. Postoperational stitch adhesion is one of the artificially occurring inflammatory adhesions, and is a complication developed by an operation at a high probability although its degree is variable. While adhesion is not problematic when no symptom is present, it sometimes causes abdominal pain, ileus, sterility and so on, and hence various measures have been taken for preventing adhesion.

Conventionally, for preventing adhesion, a method of covering the incised and sutured site with a film-like or gel-like antiadhesive material is employed. In particular, a gel-like antiadhesive material is advantageous over a film-like antiadhesive material in that it is easy to be closely adhered to the incised and sutured site, and is difficult to be peeled off, so that it can facilitate the technique in clinical scenes. As conventional gel-like antiadhesive materials, compositions containing polysaccharides such as alginic acid, carboxylic acid group-containing compounds and water (see JP 2003-153999 A) and the like have been reported.

Considering the operability in clinical scenes, the gel-like antiadhesive material desirably has high fluidity for administration to the incised and sutured site, but it desirably has low fluidity from the viewpoint of preventing adhesion. Thus, the required fluidity is contrary between the operability in clinical scenes and for the antiadhesive effect as described above. However, conventionally reported gel-like antiadhesive materials cannot adequately satisfy both the operability in clinical scenes and the antiadhesive effect because they are given in a gelled state having certain fluidity as a result of preliminary mixing a gelling agent with water.

In the context of such conventional art, it is strongly demanded to develop an antiadhesive material designed to have fluidity varying with time in such a manner that the material exhibits a gel form of high fluidity at the time of administration, and the material exhibits a gel form of low fluidity after it is administered to an incised and sutured site.

SUMMARY OF THE INVENTION

It is an object of the present invention to provide an antiadhesive material designed to have time-varying fluidity as it exhibits a gel form of high fluidity at the time of administration, and exhibits a gel form of low fluidity after it is administered to an incised and sutured site.

The present inventors made diligent efforts for solving the above-described problem, and found that a powdery antiadhesive material to be mixed with an aqueous solvent upon use, containing alginic acid and/or a salt thereof and being configured to be used after being is mixed with an aqueous solvent so that the viscosity at 37° C. is less than or equal to 70 mPas·s at the time of 5 minutes after mixing with the aqueous solvent, and the viscosity at 37° C. is more than or equal to 120 mPas·s at the time of 60 minutes after mixing with the aqueous solvent, will have high fluidity at the time of administration when it is mixed with an aqueous solvent upon use in a clinical scene, and have low fluidity after it is administered to an incised and sutured site, and thus is capable of satisfying both the excellent operability and the antiadhesive effect. The present invention was accomplished by repeating further examinations based on the above-described findings.

Specifically, the present invention provides the following aspects of the invention.

1. A powdery antiadhesive material to be mixed with an aqueous solvent upon use, containing:

alginic acid and/or a salt thereof, the antiadhesive material being mixed with the aqueous solvent upon use so that the viscosity at 37° C. is less than or equal to 70 mPas·s at the time of 5 minutes after mixing with the aqueous solvent, and the viscosity at 37° C. is more than or equal to 120 mPas·s at the time of 60 minutes after mixing with the aqueous solvent.

2. The antiadhesive material according to 1., further containing a salt of an organic acid and/or an inorganic acid and a bivalent metal.

3. The antiadhesive material according to 1. or 2., further containing a polyethylene glycol.

4. The antiadhesive material according to any one of 1. to 3., further containing an organic acid and/or an alkali metal salt thereof.

5. The antiadhesive material according to 2., wherein the salt of an organic acid and/or an inorganic acid and a bivalent metal is a calcium salt of an organic acid and/or an inorganic acid.

6. The antiadhesive material according to 4., wherein the organic acid and/or the alkali metal salt thereof is at least one selected from the group consisting of glucono-δ-lactone, gluconic acid, and an alkali metal salt of gluconic acid.

7. The antiadhesive material according to any one of 1. to 6., configured to be mixed with the aqueous solvent so that the amount of the alginic acid and/or the salt thereof contained in the antiadhesive material is 1 to 4% by weight upon use.

8. An antiadhesive gel production kit including a syringe containing the antiadhesive material according to any one of 1. to 7.

9. An antiadhesive gel production kit including a powdery antiadhesive material and an aqueous solvent, for obtaining an antiadhesive gel by mixing the powdery antiadhesive material with the aqueous solvent upon use, the powdery antiadhesive material containing alginic acid and/or a salt thereof, wherein when the powdery antiadhesive material is mixed with the aqueous solvent, the viscosity of the antiadhesive gel at 37° C. is less than or equal to 70 mPas·s at the time of 5 minutes after mixing with the aqueous solvent, and the viscosity of the antiadhesive gel at 37° C. is more than or equal to 120 mPas·s at the time of 60 minutes after mixing.

10. The antiadhesive gel production kit according to 9., including a syringe containing a powdery antiadhesive material, and a container containing an aqueous solvent.

11. The antiadhesive gel production kit according to 9., wherein in a container having two storing chambers separated by a partition that allows communication therebetween, the powdery antiadhesive material and the aqueous solvent are contained in the respective storing chambers while they are separated from each other.

12. An adhesion prevention method, including the step of mixing the antiadhesive material according to any one of 1. to 7. with an aqueous solvent, and applying the mixture to an affected site where prevention of adhesion is required.

13. Use of a powder agent containing alginic acid and/or a salt thereof for producing a powdery antiadhesive material to be mixed with an aqueous solvent upon use so that the viscosity at 37° C. is less than or equal to 70 mPas·s at the time of 5 minutes after mixing with the aqueous solvent, and the viscosity at 37° C. is more than or equal to 120 mPas·s at the time of 60 minutes after mixing with the aqueous solvent.

The antiadhesive material of the present invention is provided in a powder form, and mixed with an aqueous solvent in a clinical scene upon use to be rendered an antiadhesive gel, and administered to an incised and sutured site where prevention of adhesion is required. Since the antiadhesive gel obtained by mixing the antiadhesive material of the present invention with water becomes a gel of high fluidity at the time of 5 minutes after preparation (after mixing with the aqueous solvent), it is in a condition of easy to be administered to the incised and sutured site at the time of administration, and hence is excellent in operability in clinical scenes. Further, since the antiadhesive gel obtained by mixing the antiadhesive material of the present invention with water becomes a gel of low fluidity at the time of 60 minutes after preparation (after mixing with the aqueous solvent), it is stably fixed in the incised and sutured site where it is administered, and can exert an excellent antiadhesive effect.

When the antiadhesive material of the present invention contains a combination of a salt of an organic acid and/or an inorganic acid and a bivalent metal, a polyethylene glycol, and an organic acid and/or an alkali metal salt thereof besides alginic acid and/or a salt thereof, a homogenous gel can be prepared without occurrence of a lump when the antiadhesive material is mixed with an aqueous solvent. Therefore, the antiadhesive material can be used easily in a clinical scene without necessity of using a stirrer for preparing a gel.

Also, since the antiadhesive material of the present invention is provided and preserved in a powder form, it is less influenced by the temperature or the like in a normal preservation condition, and is excellent also in the preservation stability.

Further, by using the antiadhesive gel production kit of the present invention, it is possible to facilitate preparation of the antiadhesive gel by mixing of the powdery antiadhesive material with water. In particular, according to the antiadhesive gel production kit including a syringe containing a powdery antiadhesive material, not only preparation of the antiadhesive gel is facilitated, but also administration of the antiadhesive gel to an incised and sutured site is facilitated, and convenience in using a powdery antiadhesive material is improved.

DETAILED DESCRIPTION OF PREFERRED EMBODIMENTS

The antiadhesive material of the present invention is a powdery antiadhesive material to be mixed with water upon use, containing alginic acid and/or a salt thereof, and mixed with an aqueous solvent upon use so that the viscosity at 37° C. is less than or equal to 70 mPas·s at the time of 5 minutes after mixing with the aqueous solvent, and the viscosity at 37° C. is more than or equal to 120 mPas·s at the time of 60 minutes after mixing with the aqueous solvent. Hereinafter, the antiadhesive material of the present invention will be described in detail.

<Viscosity Characteristics>

The antiadhesive material of the present invention is in a powder form, and is used in the form of an antiadhesive gel by being mixed with an aqueous solvent upon use. The term "antiadhesive gel" used herein refers to a gel-like substance obtained by mixing the antiadhesive material of the present invention with an aqueous solvent.

Since the antiadhesive gel prepared from the antiadhesive material of the present invention is designed to have high fluidity directly after preparation, and have low fluidity after a lapse of a predetermined time, both the excellent operability and the antiadhesive effect are provided. Hereinafter, the viscosity characteristics of the antiadhesive material of the present invention will be described.

When the antiadhesive material of the present invention is mixed with a predetermined amount of the aqueous solvent, the viscosity increases with time. The antiadhesive material of the present invention is configured to have a viscosity at 37° C. of less than or equal to 70 mPas·s at the time of 5 minutes after mixing with the predetermined amount of the aqueous solvent. Thus, by exhibiting low viscosity and high fluidity up to 10 minutes after mixing with the aqueous solvent, the antiadhesive gel can be easily administered to an incised and sutured site, and can easily cover the entire incised and sutured site uniformly, and excellent operability in clinical scenes is provided.

From the viewpoint of further improving the operability in clinical scenes, a preferred viscosity at 37° C. at the time of 5 minutes after mixing with the aqueous solvent is in the range of 5 to 70 mPas·s. Particularly for use in the field of orthopedics, the viscosity is more preferably 5 to 70 mPas·s, further preferably 10 to 60 mPas·s, and particularly preferably 15 to 50 mPas·s. For use in the field of gastroenterology, the viscosity is more preferably 20 to 70 mPas·s, further preferably 30 to 70 mPas·s, and particularly preferably 50 to 70 mPas·s.

The antiadhesive material of the present invention is configured to have a viscosity at 37° C. of more than or equal to 120 mPas·s at the time of 60 minutes after mixing with the predetermined amount of the aqueous solvent. Thus, by exhibiting high viscosity and low fluidity at the time of 60 minutes after mixing with the aqueous solvent, the antiadhesive gel administered can be stably fixed to the incised and sutured site, and an excellent antiadhesive effect can be exerted.

From the viewpoint of further improving the antiadhesive effect, the viscosity at 37° C. at the time of 60 minutes after mixing with the aqueous solvent is preferably more than or equal to 300 mPas·s and more preferably more than or equal to 1000 mPas·s for use both in the fields of orthopedics and gastroenterology. The upper limit value of the viscosity at 37° C. at the time of 60 minutes after mixing with the aqueous solvent is not particularly limited, but it is, for example, 150000 mPas·s.

Further, from the viewpoint of further improving the antiadhesive effect, in addition to that the viscosities at the time of 5 minutes and 60 minutes after mixing with the aqueous solvent fall within the above-described ranges, it is desired that the antiadhesive gel at the time of 30 minutes after mixing with the aqueous solvent has a viscosity at 37° C. of less than or equal to 20000 mPas·s, preferably 10 to 10000 mPas·s, and more preferably 50 to 5000 mPas·s.

The antiadhesive material of the present invention has only to be configured to exhibit the viscosities at the time of 5 minutes and 60 minutes after mixing with the aqueous solvent satisfying the above-described ranges, however, it is desired that the viscosity at 37° C. at the time of 60 minutes after mixing with the aqueous solvent is usually 5 times or more, preferably 5 times or more, more preferably 10 times or more, more preferably 20 times or more, and more preferably 50 times or more to the viscosity at 37° C. at the time of 5 minutes after mixing with the aqueous solvent from the viewpoint of more favorably satisfying both the fluidity for making the administered antiadhesive gel spread throughout the incised and sutured site, and the excellent antiadhesive effect by fixation of the antiadhesive gel in the incised and sutured site. A non-limitative example of the upper limit value of the ratio of the viscosity at 37° C. at the time of 60 minutes after mixing with the aqueous solvent to the viscosity at the time of 5 minutes after mixing therewith is 10000 times, preferably 5000 times, more preferably 2500 times, more preferably 1000 times.

The antiadhesive material of the present invention has only to be configured to exhibit the viscosities at the time of 5 minutes and 60 minutes after mixing with the aqueous solvent satisfying the above-described ranges, however, it is desired that the increasing speed of viscosity peaks at 30 minutes or later, preferably at 35 to 60 minutes, and further preferably 45 to 60 minutes after mixing with the aqueous solvent from the viewpoint of more favorably satisfying both the fluidity of the antiadhesive gel before administration and the antiadhesive effect after administration.

In the present invention, the viscosity is measured under the following measurement conditions.

(1) To a 10 ml-volume glass test tube, a powdery antiadhesive material and an aqueous solvent are added in a specified mixing ratio, so that the amount of the aqueous solvent is 5 mL, and the mixture is stirred for 20 seconds by using a vortex mixer, to prepare an antiadhesive gel. This operation is conducted under the temperature condition of 37° C.

(2) Letting the end of stirring be 0 minute, the antiadhesive gel is left still under the temperature condition of 37° C., sampled at predetermined time points, and measured for the viscosity at 37° C. under the following measurement conditions.

Device: Viscosity and viscoelasticity measuring device (rheometer)
Temperature control unit: Peltier plate
Measurement geometry: Parallel plate of 35 mm in diameter
Gap: 1 mm
Sample amount: 1 mL
Applied stress: 11.90 Pa
Frequency: 0.5000 Hz
Angular velocity: 3.142 rad/s The above-described increasing speed of viscosity is determined by measuring the viscosity over time in the above-described conditions, and calculating an increase of viscosity every 5 minutes from mixing with the aqueous solvent.

The above-described viscosity characteristics of the antiadhesive gel can be provided by incorporating alginic acid and/or a salt thereof as a gelling agent, appropriately setting the content thereof and other ingredients, and appropriately setting the mixing ratio with the aqueous solvent upon use in the antiadhesive material of the present invention.

<Ingredients>

Alginic Acid and/or a Salt Thereof

The antiadhesive material of the present invention contains alginic acid and/or a salt thereof (hereinafter, simply referred to as a component (A)) as a gelling agent.

A salt of alginic acid is not particularly limited as far as it is pharmaceutically acceptable, and examples include alkali metal salts such as sodium salts and potassium salts, and alkaline earth metal salts such as calcium salts.

The weight average molecular weight of alginic acid and/or a salt thereof is not particularly limited as far as the above-described viscosity characteristics are provided, and is, for example, 50,000 to 600,000, preferably 50,000 to 500,000 and more preferably 80,000 to 500,000.

Alginic acid and/or a salt thereof is commercially available. Examples of the commercially available products of alginic acid and/or a salt thereof include KIMICA ALGIN High•G series IL-6G (1 w/v % aqueous solution, viscosity at 20° C.: 50 to 80 mPa·s; weight average molecular weight: about 680,000), I-1G (1 w/v % aqueous solution, viscosity at 20° C.: 100 to 200 mPa·s; weight average molecular weight: about 720,000), I-3G (1 w/v % aqueous solution, viscosity at 20° C.: 300 to 400 mPa·s; weight average molecular weight: about 800,000) and so on; KIMICA ALGIN I series IL-6 (1 w/v % aqueous solution, viscosity at 20° C.: 50 to 80 mPa·s; weight average molecular weight: about 690,000), I-1 (1 w/v % aqueous solution, viscosity at 20° C.: 80 to 200 mPa·s; weight average molecular weight: about 860,000), 1-3 (1 w/v % aqueous solution, viscosity at 20° C.: 300 to 400 mPa·s; weight average molecular weight: about 770,000), I-5 (1 w/v % aqueous solution, viscosity at 20° C.: 500 to 600 mPa·s; weight average molecular weight: about 800,000), 1-8 (1 w/v % aqueous solution, viscosity at 20° C.: 800 to 900 mPa·s; weight average molecular weight: about 790,000), IL-1 (1 w/v % aqueous solution, viscosity at 20° C.: about 15 mPa·s; weight average molecular weight: about 260,000), IL-2 (1 w/v % aqueous solution, viscosity at 20° C.: 20 to 50 mPa·s; weight average molecular weight:

about 580,000) and so on; and KIMICA ALGIN ULV series ULV-5 (10 w/v % aqueous solution, viscosity at 20° C.: 500 to 600 mPa·s; 1 w/v % aqueous solution, viscosity at 20° C.: about 4 mPa·s; weight average molecular weight: about 80,000), ULV-10 (1 w/v % aqueous solution, viscosity at 20° C.: about 7 mPa·s; weight average molecular weight: about 90,000), ULV-20 (1 w/v % aqueous solution, viscosity at 20° C.: about 10 mPa·s; weight average molecular weight: about 200,000) and so on (all of these are available from KIMICA Corporation). Among these, I-1G, I-3G, I-1, IL-1, ULV-5, ULV-10, ULV-20 and so on are preferred.

In the antiadhesive material of the present invention, the one selected from alginic acid and a salt thereof may be used singly, or in combination of two or more thereof. Among the alginic acid and a salt thereof, alginic acid and an alkali metal salt thereof are preferred, and a sodium salt of alginic acid is more preferred from the viewpoint of further improving both the operability in clinical scenes and the antiadhesive effect.

The content of the component (A) in the antiadhesive material of the present invention may be appropriately set so that the above-described viscosity characteristics are provided, and is, for example, 1 to 50% by weight. From the viewpoint of providing the above-described viscosity characteristics more favorably and further improving both the operability in clinical scenes and the antiadhesive effect, the content of the component (A) is preferably 5 to 25% by weight.

Salt of Organic Acid and/or Inorganic Acid and Bivalent Metal

The antiadhesive material of the present invention may contain a salt of an organic acid and/or an inorganic acid and a bivalent metal (hereinafter, also referred to simply as a component (B)). When a salt of an organic acid and/or an inorganic acid and a bivalent metal is contained, it is possible to further improve both the operability in clinical scenes and the antiadhesive effect while satisfying the above-described viscosity characteristics.

The salt of an organic acid and/or an inorganic acid and a bivalent metal used in the present invention is not particularly limited as far as it is pharmaceutically acceptable. Examples of the acid constituting the salt include organic acids such as gluconic acid, lactic acid, oxalic acid, citric acid and acetic acid; and inorganic acids such as sulfuric acid, hydrochloric acid, phosphoric acid and nitric acid. Examples of the bivalent metal constituting the salt include barium, magnesium, calcium, iron and so on. Among these bivalent metals, calcium is preferred.

Concrete examples of the salt of an organic acid and/or an inorganic acid and a bivalent metal include calcium lactate, calcium gluconate, calcium sulfate, calcium citrate, and dicalcium phosphate (calcium monohydrogen phosphate dihydrate). Among these, from the viewpoint of providing the above-described viscosity characteristics in a more preferred range, a water-insoluble salt is preferred. Concrete examples of the water-insoluble salt include calcium sulfate, calcium citrate, calcium monohydrogen phosphate dihydrate, and calcium carbonate. The term "water-insoluble" used herein corresponds to "slightly soluble" to "practically insoluble" as defined in the 16th Edition of the Japanese Pharmacopoeia. In other words, it means that 100 mL or more of a solvent is required for dissolving 1 g of a solute (salt of an organic acid and/or an inorganic acid and a bivalent metal).

For providing the above-described viscosity characteristics, as the salt of an organic acid and/or an inorganic acid and a bivalent metal, dicalcium phosphate, calcium monohydrogen phosphate dihydrate, and calcium carbonate are preferred.

These salts of an organic acid and/or an inorganic acid and a bivalent metal may be used singly or in combination of two or more thereof.

The content of the salt of an organic acid and/or an inorganic acid and a bivalent metal in the antiadhesive material of the present invention is, for example, 0.1 to 50% by weight, preferably 1 to 20% by weight, and more preferably 1 to 10% by weight.

While the ratio between the component (A) and the component (B) in the antiadhesive material of the present invention is not particularly limited, since the gelling speed increases and the gel strength tends to be higher as the ratio of the component (B) to the component (A) increases, the ratio is appropriately set to provide the above-described viscosity characteristics in consideration of these behaviors. For example, it is just required to satisfy the ratio of 1 part by weight or less of the component (B) per 1 part by weight of the component (A). In particular, from the viewpoint of providing the above-described viscosity characteristics in a more preferred range, and further improving both the operability in clinical scenes and the antiadhesive effect, the amount of the component (B) per 1 part by weight of the component (A) is preferably 0.01 to 1 part by weight, more preferably 0.02 to 1 part by weight, and particularly preferably 0.03 to 0.3 parts by weight.

Polyethylene Glycol

The antiadhesive material of the present invention may contain a polyethylene glycol (hereinafter, also referred to simply as a component (C)). By containing a polyethylene glycol together with the component (A) and the component (B) in the antiadhesive material of the present invention, it becomes possible to prepare a homogenous antiadhesive gel without occurrence of a lump at the time of mixing with the aqueous solvent while satisfying the above-described viscosity characteristics.

The polyethylene glycol used in the present invention desirably assumes a solid form at normal temperatures, and has an average molecular weight of, for example, about 1000 or more, preferably about 3000 or more, concretely about 1000 to about 20000, and preferably about 4000 to about 20000. When the average molecular weight of the polyethylene glycol is less than 1000, the polyethylene glycol does not assume a solid form at normal temperatures, and when the average molecular weight exceeds 20000, the polyethylene glycol becomes difficult to be handled because of the increased viscosity. Here, the average molecular weight of the polyethylene glycol is a value measured by the "macrogol 400" average molecular weight method in the 16th Edition of the Japanese Pharmacopoeia.

Concrete examples of the polyethylene glycol include macrogol 1000, macrogol 1500, macrogol 1540, macrogol 3000, macrogol 3350, macrogol 4000, macrogol 6000, macrogol 8000, macrogol 20000 and so on listed as preparation raw materials on the 16th Edition of the Japanese Pharmacopoeia and pharmaceutical additives. Among these, macrogol 3350, macrogol 4000, macrogol 6000, and macrogol 20000 are preferred, and macrogol 3350 and macrogol 4000 are more preferred from the viewpoint of providing the above-described viscosity characteristics in more preferred ranges, and further improving both the operability in clinical scenes and the antiadhesive effect.

These polyethylene glycols may be used singly or in combination of two or more thereof.

In the antiadhesive material of the present invention, the polyethylene glycol is contained preferably as a matrix base material or in the form of covering other ingredients. When it is contained as a matrix base material or in the form of covering other ingredients, it is possible to prevent occurrence of a lump at the time of mixing with water more effectively, and to control the dissolution rate of other ingredients by utilizing the dissolution rate of the polyethylene glycol itself, so that it becomes possible to provide the above-described viscosity characteristics in more preferred ranges.

The content of the component (C) in the antiadhesive material of the present invention is, for example, 1 to 99% by weight, preferably 20 to 99% by weight, and more preferably 50 to 80% by weight.

Organic Acid and/or Alkali Metal Salt Thereof

Further, the antiadhesive material of the present invention may contain an organic acid and/or an alkali metal salt thereof (hereinafter, also referred to simply as a component (D)). In the antiadhesive material of the present invention, by containing an organic acid and/or an alkali metal salt thereof, it is possible to provide the above-described viscosity characteristics in more preferred ranges, and to further improve both the operability in clinical scenes and the antiadhesive effect.

Examples of the organic acid used in the present invention include, but are not particularly limited to, glucono-δ-lactone, gluconic acid, glucuronic acid, galacturonic acid, oxalic acid, citric acid, and acetic acid. Further, examples of the salt with an organic acid include sodium salts and potassium salts. Among these, alkali metal salts of glucono-δ-lactone, gluconic acid, and gluconic acid are preferred, and sodium gluconate and glucono-δ-lactone are further preferred from the viewpoint of providing the above-described viscosity characteristics in more preferred ranges, and further improving both the operability in clinical scenes and the antiadhesive effect. Glucono-δ-lactone is a compound that is to be hydrolyzed into gluconic acid upon contact with water to exhibit acidity.

These organic acids and alkali metal salts thereof may be used singly or in combination of two or more thereof.

The content of the component (D) in the antiadhesive material of the present invention is, for example, 1 to 60% by weight, preferably 2 to 50% by weight, and more preferably 3 to 15% by weight.

When the antiadhesive material of the present invention contains the component (B) and the component (D), the mixing ratio between these components is not particularly limited, however, from the viewpoint of providing the above-described viscosity characteristics in more preferred ranges, and further improving both the operability in clinical scenes and the antiadhesive effect, the amount of the component (D) is 0.01 to 80 parts by weight, preferably 2 to 50 parts by weight, and further preferably 3 to 30 parts by weight per 1 part by weight of the component (B).

Other Ingredients

The antiadhesive material of the present invention may contain pharmacological components such as antibacterial agents, antibiotics, anti-inflammatory agents, blood circulation improvers, steroids, enzyme inhibitors, growth factors, and various vitamins as needed for the purpose of enhancing the therapeutic effect and preventing microbial infection, in addition to the above-described components. Since the antiadhesive material of the present invention remains in the incised and sutured site to which it is applied for a certain period, it can be used as a sort of drug delivery systems intended for sustained release of pharmacological components by containing the above-described pharmacological components.

Further, the antiadhesive material of the present invention may contain additives such as an excipient, a binder, a lubricant, a pH adjuster, a buffer, an antiseptic, an antioxidant, a coloring agent, and a dehumidifying agent as needed.

Preferred Combination of Ingredients

In the antiadhesive material of the present invention, ingredients other than the above-described component (A) are not particularly limited as far as the antiadhesive material contains the above-described component (A), and the preparation prescription and the use form are set so that the above-described viscosity characteristics develop, however, as a preferred combination of ingredients for satisfying the above-described viscosity characteristics, the form of containing the components (A) to (C), and more preferably the form of containing the components (A) to (D) are recited.

Shape

The particle diameter of the antiadhesive material of the present invention is not particularly limited as far as the antiadhesive material is powdery, however, from the viewpoint of realizing better solubility with the aqueous solvent at the time of mixing, the particle diameter measured by sifting is, for example, about 200 to 2000 μm, and preferably about 355 to 1000 μm.

Preparation Method

The antiadhesive material of the present invention is prepared by mixing the component (A), and the components (B) to (D) that are mixed as needed, and other pharmacological components and additives, and preparing the mixture into a powder. Concretely, when the antiadhesive material of the present invention contains the component (C), the following methods can be recited as preferable examples of the following preparation methods.

A first step of dissolving the component (C); a second step of adding and mixing the component (A), and the component (B), the component (D) and other pharmacological components and additives as needed to the solution of the component (C) obtained in the first step, and a third step of solidifying the mixture obtained in the second step and forming the mixture into a powder.

Dissolution of the component (C) in the first step can be achieved, for example, by a method of dissolving under heating, or a method of dissolving in a solvent. When the component (C) is dissolved under heating, the temperature condition is appropriately set according to the kind of the component (C) to be used, and is, for example, 50 to 90° C., and is preferably 60 to 80° C. When the component (C) is dissolved in a solvent, the component (C) may be mixed, for example, with a solvent such as a solution of 90 to 99 volume % ethanol in water, at a concentration of about 5 to 20% by weight. When the content of the component (C) in the pharmaceutical composition of the present invention is relatively large (for example, for use as an antiadhesive medical material), the first step is preferably conducted by dissolution under heating, and when the content of the component (C) is relatively small (for example, for use as a hemostatic), the first step is preferably conducted by dissolution in a solvent.

When the component (C) is dissolved in a solvent in the first step, the solvent is removed at the time of mixing or after mixing in the second step. Forming into a desired shape in the third step can be achieved by known forming methods such as grinding and granulation.

The antiadhesive material of the present invention is desirably sterilized because it will be applied to a living body. Examples of the sterilizing method include, but are not particularly limited to, EOG sterilization, electron beam sterilization, γ-ray sterilization, and ultraviolet irradiation, and preferred examples include electron beam sterilization, EOG sterilization and γ-ray sterilization from the viewpoint of keeping the stability of alginic acid and/or a salt thereof.
Use Form The antiadhesive material of the present invention is provided in a powder form, and mixed with an aqueous solvent upon use in a clinical scene, and used in the form of an antiadhesive gel.

The aqueous solvent to be used in making the antiadhesive material of the present invention into an antiadhesive gel is not particularly limited as far as it is a liquid agent containing water as a solvent and is pharmaceutically acceptable, and for example, purified water, saline, Ringer's solution, lactate Ringer's solution and the like are recited. Among these, purified water is preferred.

The mixing ratio between the antiadhesive material of the present invention and the aqueous solvent may be appropriately set so that the above-described viscosity characteristics are provided, and it may be concretely set so that the antiadhesive material of the present invention is mixed with the aqueous solvent to give a concentration of the component (A) contained in the antiadhesive material of the present invention of usually 1 to 4% by weight, and preferably 1 to 3% by weight in the prepared antiadhesive gel. More concretely, for use in the field of orthopedics, it may be set so that the antiadhesive material of the present invention is mixed with the aqueous solvent to give a concentration of the component (A) of preferably 1 to 3% by weight, more preferably 1.5 to 3% by weight, and particularly preferably 1.5 to 2.5% by weight, whereas for use in the field of gastroenterology, it may be set so that the antiadhesive material of the present invention is mixed with the aqueous solvent to give a concentration of the component (A) of preferably 3 to 4% by weight.

When the antiadhesive material of the present invention contains the components (A) to (C), or the components (A) to (D), for providing the above-described viscosity characteristics, the mixing ratio may be set so that the antiadhesive material of the present invention is mixed with the aqueous solvent to give a concentration of the antiadhesive material of the present invention of usually 5 to 20% by weight, and preferably 5 to 15% by weight in the prepared antiadhesive gel. More concretely, when the antiadhesive material of the present invention contains the components (A) to (C), or the components (A) to (D), it may be set so that the antiadhesive material of the present invention is mixed with the aqueous solvent to give a concentration of the antiadhesive material of the present invention of preferably 5 to 15% by weight, more preferably 6 to 15% by weight or 7.5 to 15% by weight, and particularly preferably 6 to 12.5% by weight or 7.5 to 12.5% by weight in the field of orthopedics; and a concentration of preferably 10 to 20% by weight, and more preferably 15 to 20% by weight in the field of gastroenterology.

The antiadhesive material of the present invention is mixed with water to be prepared into an antiadhesive gel, and then the antiadhesive gel is administered to an affected site (incised and sutured site) where prevention of adhesion is required. Since the antiadhesive gel that is obtained by mixing the antiadhesive material of the present invention with an aqueous solvent exhibits a gel form of high fluidity for 5 minutes after preparation (after mixing with the aqueous solvent), it is desired to be administered to the affected site in 5 minutes after preparation. The method for administering the antiadhesive gel prepared from the antiadhesive material of the present invention is not particularly limited, and it may be applied to the affected site, for example, with the use of a syringe, a brush or the like.

The administration amount of the antiadhesive gel prepared from the antiadhesive material of the present invention may be appropriately set according to the condition of the affected site, and is, for example, in such a range that the amount of the antiadhesive gel is about 0.005 to 0.1 g per 1 $cm^2$ of the affected site where prevention of adhesion is required.

The body site to which the antiadhesive material of the present invention is applied is not particularly limited as far as it is the site where prevention of adhesion is required, and for example, it may be sites in the field of gastroenterology such as intraperitoneal organs, or may be sites in the field of orthopedics such as tendon, nerve, and joint. In particular, in the filed orthopedics such as tendon, nerve, and joint having fine tissue structures, it is difficult to apply an antiadhesive material throughout the tissue by the use of a conventional antiadhesive material. In contrast, the antiadhesive gel prepared by using the antiadhesive material of the present invention is advantageous in that it can be applied throughout such a site having a fine tissue structure because it has low viscosity and high fluidity at the time of administration.

<Antiadhesive Gel Production Kit-1>

By providing the antiadhesive material in such a form that it is contained in a syringe and is ready to be mixed with water in the syringe upon use, an antiadhesive gel can be prepared in a simple and easy way in a clinical scene. That is, the present invention provides a gel production kit including a syringe containing the antiadhesive material.

The syringe used in the gel production kit of the present invention is not particularly limited, and for example, the one having a syringe body having a nozzle at its tip end, a gasket that is inserted into the syringe body and is slidable in the axial direction of the syringe body, and a plunger for displacing the gasket can be recited. The capacity of the syringe body may be such a size that can contain the antiadhesive gel in the amount corresponding to at least a single dose, and is, for example, 1 to 20 ml, and preferably 2 to 10 ml.

The gel production kit of the present invention may be so configured that the antiadhesive material is contained in the syringe, and a predetermined amount of the aqueous solvent is inserted into the syringe upon use to prepare an antiadhesive gel, or so configured that two different sections are provided in the syringe, and predetermined amounts of the antiadhesive material and the aqueous solvent are respectively contained in the different sections to be ready for mixing upon use in the syringe. In the latter case, concretely, an antiadhesive material storing chamber containing the antiadhesive material and an aqueous solvent storing chamber containing an aqueous solvent are included in the syringe while they are separated from each other, to allow mixing of the antiadhesive material with the aqueous solvent upon use. The syringe having two different sections that are separated from each other, and designed to allow mixing of the contents of the two sections upon use is known as disclosed, for example, in JP 2001-104482 A. For mixing the antiadhesive material with the aqueous solvent in a syringe, the syringe may be shaken back and forth or right and left in the condition that the antiadhesive material and the aqueous solvent are in contact with each other in the syringe.

In the gel production kit of the present invention, the amount of the antiadhesive material contained in the syringe has to be an amount corresponding to at least a single dose, and is concretely 0.1 to 20 g or 0.1 to 2 g, and preferably 0.2 to 10 g or 0.2 to 1 g. When the antiadhesive material and the aqueous solvent are contained in different sections in the syringe, the amount of the aqueous solvent contained in the syringe may be appropriately set so that desired viscosity characteristics are satisfied in consideration of the above-described mixing ratio between the antiadhesive material and the aqueous solvent.

In the gel production kit of the present invention, an applicator (tubular needle) for delivering an antiadhesive gel to an affected site may be attached to the nozzle at the tip end of the syringe body may, or the nozzle may be configured to allow attachment of the applicator. The structure of the applicator is not particularly limited as far as it is capable of delivering the antiadhesive gel in the syringe to an affected site, however, from the viewpoint of the convenience of administration to the affected site, it is preferably formed of an elastic material made of a resin. When the applicator is formed of an elastic material made of a resin, the shape thereof is not particularly limited, however, from the viewpoint of further improving the convenience of administration to an affected site, preferably, the caliber is about 0.1 to 5 mm and the length is about 1 to 10 cm.

Figure 1:
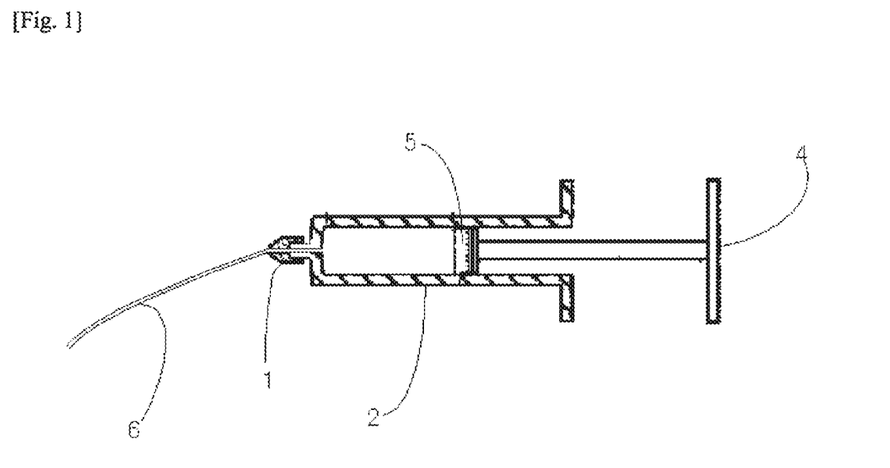
FIG. 1 is a drawing illustrating one form of a syringe used in a gel production kit of the present invention.

One embodiment of the syringe used in the gel production kit of the present invention is illustrated in FIG. 1. The syringe illustrated in FIG. 1 includes a syringe body 2 having a nozzle 1 at its tip end part, a gasket 3 that is to be inserted in the syringe body 2 and is slidable in the axial direction of the syringe body, and a plunger 4 provided for displacing the gasket, and an applicator 5 made of an elastic resin is attached to the nozzle 1. The applicator 5 may be provided in a detached state from the nozzle 1, and may be attached to the nozzle 1 upon use.

<Antiadhesive Gel Production Kit-2>

The present invention also provides an antiadhesive gel production kit containing the antiadhesive material and the aqueous solvent, configured to obtain an antiadhesive gel by mixing the powdery antiadhesive material with the aqueous solvent upon use.

Compositions of the antiadhesive material and the aqueous solvent in the antiadhesive gel production kit, the mixing ratio between these and so on are as described above.

The antiadhesive gel production kit is not particularly limited as far as it is provided in the condition that the antiadhesive material is not mixed with the aqueous solvent, and the antiadhesive material is mixed with the aqueous solvent upon use, and concretely, an embodiment in which the kit includes an antiadhesive material contained in the syringe, and an aqueous solvent contained in a container that is different from the syringe (exemplary embodiment 1); an embodiment in which an antiadhesive material and an aqueous solvent are contained in different storing chambers in a container having two storing chambers separated by a partition that allows communication therebetween (exemplary embodiment 2) and so on are recited.

The structure and the like of the syringe used in the exemplary embodiment 1 are as described above.

The container used in the exemplary embodiment 2 may be a container having two storing chambers separated by a partition that allows communication therebetween, and designed to make the two storing chambers communicate with each other upon use by power applied from outside such as pressing or folding. The structure of such a container is known in the art, and those having a bag shape, a vial shape and so on are known. Concretely, a container having a bag shape is disclosed in JP 4-364851 A, and a container having a vial shape is disclosed in JP 2005-6945 A. As the container having a vial shape, it is also known that two vial shape containers are connected using a double-ended needle disclosed in JP 4-364851 A and so on. Since such a container having a bag shape or a container having a vial shape can contain 0.1 to 20 g, preferably 0.2 to 10 g of an antiadhesive material, it is desirable for the case of using an antiadhesive material of such an amount that cannot be contained in the syringe or the like. In the exemplary embodiment 2, since the antiadhesive material and the aqueous solvent are provided while they are contained in advance in a single container, it is advantageous also in that the antiadhesive gel can be conveniently prepared in a clinical scene.

EXAMPLES

Hereinafter, the present invention will be described in detail based on examples and so on, however, the present invention will not be restricted by these examples.

Test Example 1. Evaluation of Viscosity Characteristics

Preparation of Antiadhesive Material

To macrogol 4000 (product of Sanyo Chemical Industries, Ltd.) melted at about 70° C., sodium alginate, calcium hydrogen phosphate dihydrate (product of Wako Pure Chemical Industries, Ltd.) and glucono-δ-lactone (product of Spectrum Chemical Mfg. Corp. USP) were added, and mixed thoroughly using a stirrer, and then cooled naturally. Thereafter, the mixture was ground, and sieved through Japanese Pharmacopoeia No. 22 sieve (sieve opening 710 μm) to obtain a powdery antiadhesive material having passed through the sieve. Mixing amounts of components are as described in Table 1 below.

TABLE 1

|  | Composition |
| --- | --- |
| Sodium alginate | 20 |
| Calcium hydrogen phosphate dihydrate | 2 |
| Macrogol 4000 | 68 |
| Glucono-δ-lactone | 10 |
| Total | 100 |

In this table, the unit of quantity of each ingredient is % by weight.

As sodium alginate, a mixture of 90 parts by weight of KIMICA ALGIN ULV series ULV-5 (10 w/v % aqueous solution, viscosity at 20° C.: 500 to 600 mPa·s; product of KIMICA Corporation) and 10 parts by weight of KIMICA ALGIN I series I-1 (1 w/v % aqueous solution, viscosity at 20° C.: 80 to 200 mPa·s; weight average molecular weight: about 860,000; product of KIMICA Corporation) was used.

Measurement of Viscosity after Mixing with Water

For each antiadhesive material obtained in the above, viscosity change after mixing with purified water was measured. Concretely, to a 10 ml-volume test tube containing 5 ml of purified water, each antiadhesive material was added in a concentration as shown in Table 2, and stirred for 20 seconds using a vortex mixer, to prepare an antiadhesive gel (Prescriptions 1 to 6). Letting the end of stirring be 0 minute, the antiadhesive gel was left still for 60 minutes under the temperature condition of 37° C., and the viscosity at 37° C. was measured over time under the following measurement conditions. Every operation in this measurement was conducted under the temperature condition of 37° C.

Figure 2:
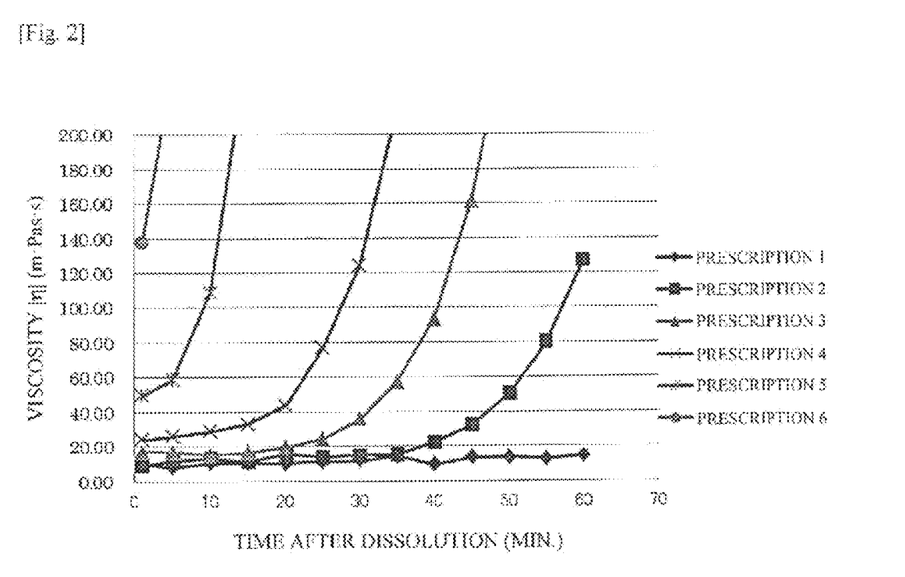
FIG. 2 is a chart illustrating time-series measurement results of the viscosity of the antiadhesive gel when water was used as the aqueous solvent in Test Example 1.
Figure 3:
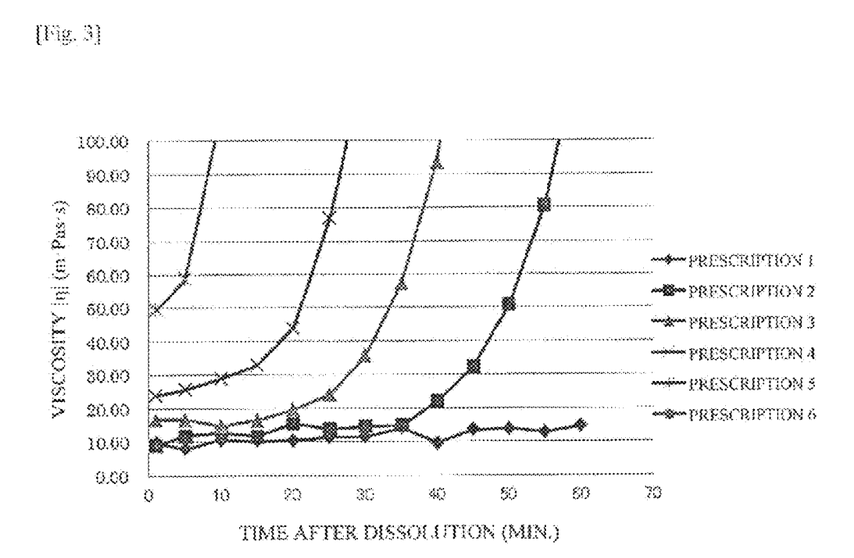
FIG. 3 is a chart illustrating time-series measurement results of the viscosity of the antiadhesive gel when saline or lactate Ringer solution was used as the aqueous solvent in Test Example 1.

Device: Viscosity and viscoelasticity measuring device (rheometer)
Temperature control unit: Peltier plate
Measurement geometry: Parallel plate of 35 mm in diameter
Gap: 1 mm
Sample amount: 1 mL
Applied stress: 11.90 Pa
Frequency: 0.5000 Hz
Angular velocity: 3.142 rad/s The obtained result is shown in Table 2, and FIGS. 2 and 3. FIGS. 2 and 3 are charts showing the same result in different scales of the vertical axis (viscosity). In the present test, it was confirmed that in any antiadhesive material, solubility in purified water is excellent and a homogenous gel is formed when mixed with purified water without occurrence of a lump.

It was also confirmed that the antiadhesive gels prepared in Prescriptions 2 to 5 are suited for discharging from the syringe and has fluidity sufficient to spread throughout the application site at the time of 5 minutes after preparation. It was also confirmed that the antiadhesive gels prepared in Prescriptions 2 to 5 each become a gel having low fluidity that is easily fixed to the applied site at the time of 60 minutes after preparation.

solution (Lactec Injection, Otsuka Pharmaceutical Factory, Inc.) was measured. Concretely, to a 10 ml-volume test tube containing 5 ml of saline or lactate Ringer solution, each antiadhesive material was added in a concentration as shown in Table 3, and stirred for 20 seconds using a vortex mixer, to prepare an antiadhesive gel (Prescriptions 7 to 10). Letting the end of stirring be 0 minute, the antiadhesive gel was left still for 60 minutes under the temperature condition of 37° C., and the viscosity at 37° C. was measured in the same measurement conditions as described above. Every operation in this measurement was conducted under the temperature condition of 37° C.

Figure 4:
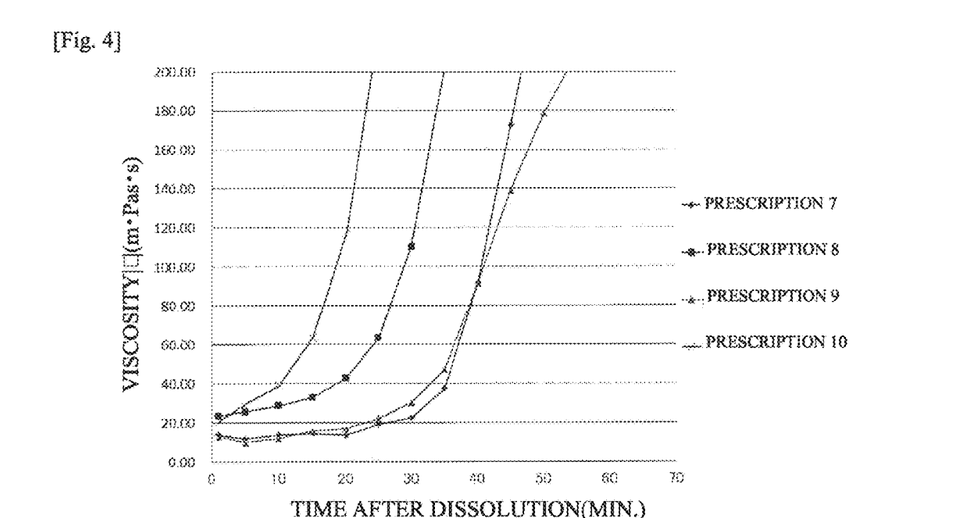
FIG. 4 is a chart illustrating time-series measurement results of the viscosity of the antiadhesive gel when saline or lactate Ringer solution was used as the aqueous solvent in Test Example 1.
Figure 5:
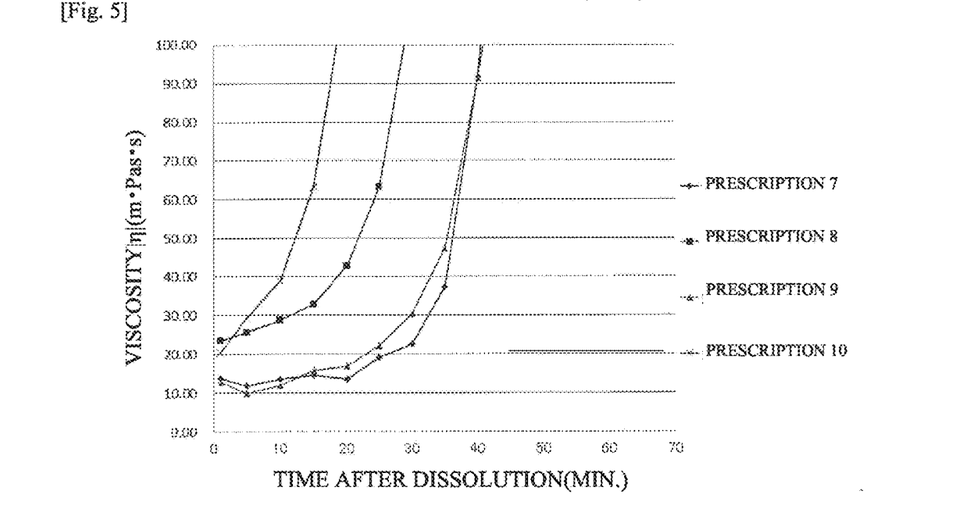
FIG. 5 is a chart illustrating time-series measurement results of the viscosity of the antiadhesive gel when saline or lactate Ringer solution was used as the aqueous solvent in Test Example 1.

The obtained result is shown in Table 3, and FIGS. 4 and 5. FIGS. 4 and 5 are charts showing the same result in different scales of the vertical axis (viscosity). In the present test, it was confirmed that in any antiadhesive material, solubility in saline or lactate Ringer solution is excellent and a homogenous gel is formed when mixed with saline or lactate Ringer solution without occurrence of a lump.

It was also confirmed that the antiadhesive gels prepared in Prescriptions 7 to 10 are suited for discharging from the syringe and has fluidity sufficient to spread throughout the application site at the time of 5 minutes after preparation. It

TABLE 2

| | | Viscosity \|η\| (mPas · s) | | | | | |
|---|---|---|---|---|---|---|---|
| | | Prescription 1 | Prescription 2 | Prescription 3 | Prescription 4 | Prescription 5 | Prescription 6 |
| Adding concentration of antiadhesive material (antiadhesive material concentration in antiadhesive gel) (% by weight) | | 2.5 | 5.0 | 7.5 | 10.0 | 15.0 | 25.0 |
| Adding concentration in terms of sodium alginate (sodium alginate concentration in antiadhesive gel) (% by weight) | | 0.5 | 1.0 | 1.5 | 2.0 | 3.0 | 5.0 |
| Mixed aqueous solvent | | Purified water | Purified water | Purified water | Purified water | Purified water | Purified water |
| Leaving time (min.) | 1 | 17.85 | 9.12 | 16.81 | 23.97 | 49.54 | 137.99 |
| | 5 | 7.94 | 11.81 | 16.74 | 25.81 | 58.70 | 235.37 |
| | 10 | 11.65 | 12.97 | 14.76 | 28.95 | 108.47 | 995.41 |
| | 15 | 8.77 | 11.53 | 16.51 | 33.03 | 247.28 | 3467.55 |
| | 20 | 11.38 | 15.53 | 19.54 | 44.00 | 632.58 | 13442.60 |
| | 25 | 13.42 | 13.84 | 24.26 | 76.75 | 2567.36 | 17832.60 |
| | 30 | 11.14 | 14.70 | 35.75 | 123.94 | 19058.75 | 26016.86 |
| | 35 | 12.90 | 14.93 | 57.38 | 212.17 | 39953.15 | 35129.71 |
| | 40 | 13.24 | 22.16 | 93.45 | 405.37 | 63588.55 | 41509.39 |
| | 45 | 16.79 | 32.26 | 161.29 | 733.71 | 83350.95 | 49686.67 |
| | 50 | 15.61 | 50.83 | 266.79 | 1435.88 | 107608.39 | 61110.28 |
| | 55 | 16.81 | 80.44 | 452.31 | 4070.62 | 119479.01 | 72530.30 |
| | 60 | 21.41 | 126.85 | 760.61 | 12596.43 | 124173.60 | 80394.44 |
| Ratio of viscosity at 60 minutes after mixing to viscosity at 5 minutes after mixing | | 2.7 times | 10.7 times | 45.4 times | 488.0 times | 2115.4 times | 341.6 times |
| Time at which increasing speed of viscosity peaked after mixing | | 55-60 min. | 55-60 min. | 55-60 min. | 55-60 min. | 45-50 min. | 45-50 min. |

Measurement of Viscosity after Mixing with Saline or Lactate Ringer Solution

For each antiadhesive material obtained in the above, viscosity change after mixing with saline or lactate Ringer was also confirmed that the antiadhesive gels prepared in Prescriptions 7 to 10 each become a gel having low fluidity that is easily fixed to the applied site at the time of 60 minutes after preparation.

TABLE 3

| | Viscosity \|η\| (mPas · s) | | | |
|---|---|---|---|---|
| | Prescription 7 | Prescription 8 | Prescription 9 | Prescription 10 |
| Adding concentration of antiadhesive material (antiadhesive material concentration in antiadhesive gel) (% by weight) | 5.0 | 10.0 | 5.0 | 10.0 |

TABLE 3-continued

|  |  | Viscosity $|\eta|$ (mPas · s) | | | |
| --- | --- | --- | --- | --- | --- |
|  |  | Prescription 7 | Prescription 8 | Prescription 9 | Prescription 10 |
| Adding concentration in terms of sodium alginate (sodium alginate concentration in antiadhesive gel) (% by weight) | | 1.0 | 2.0 | 1.0 | 2.0 |
| Mixed aqueous solvent | | Saline | Saline | lactate Ringer solution | lactate Ringer solution |
| Leaving time (min.) | 1 | 13.81 | 23.48 | 12.80 | 20.48 |
|  | 5 | 11.85 | 25.58 | 9.97 | 29.24 |
|  | 10 | 13.57 | 28.76 | 11.96 | 38.85 |
|  | 15 | 14.50 | 32.84 | 15.77 | 63.22 |
|  | 20 | 13.58 | 42.82 | 16.92 | 116.91 |
|  | 25 | 19.17 | 63.41 | 22.25 | 223.40 |
|  | 30 | 22.54 | 110.45 | 30.39 | 395.18 |
|  | 35 | 37.37 | 202.24 | 47.36 | 613.26 |
|  | 40 | 91.66 | 341.68 | 91.47 | 836.32 |
|  | 45 | 172.54 | 520.33 | 139.23 | 1046.61 |
|  | 50 | 257.83 | 692.27 | 178.58 | 1220.90 |
|  | 55 | 332.27 | 820.35 | 210.15 | 1338.07 |
|  | 60 | 374.01 | 891.00 | 234.18 | 1420.42 |
| Ratio of viscosity at 60 minutes after mixing to viscosity at 5 minutes after mixing | | 31.6 times | 34.8 times | 23.5 times | 48.6 times |
| Time at which increasing speed of viscosity peaked after mixing | | 45-50 min | 40-45 min | 40-45 min | 35-40 min |

Test Example 2. Tendon Antiadhesive Effect

Using a male rat (Crlj: WI) (available from Charles River Laboratories Japan, Inc.), the antiadhesive effect on the tendon was evaluated. Concretely, after vertically cutting open the membranous tendon sheath of the rat plantar region, flexor digitorum profundus was exposed and cut into a half size to prepare a tendon injured model rat. Separately, an antiadhesive material having a composition shown in Table 1 was added to purified water so that the concentration was 2.5% by weight (Prescription 1), 5% by weight (Prescription 2), 10% by weight (Prescription 4), 15% by weight (Prescription 5), and 25% by weight (Prescription 6) and shaken thoroughly to prepare an antiadhesive gel, and in 1 minute from the end of stirring, 50 µL, of the antiadhesive gel was administered to the half-cut operated site and the vicinity thereof of the tendon injured model rat. For preventing the half-cut tendon from breaking due to motion of the rat itself, the rat was fed for four weeks in the condition that the sciatic nerve was cut off and the automatism was restricted. After four weeks, the leg was separated from the ankle in the condition that only the flexor digitorum longus muscle was left. A load of 60 g was applied to the flexor digitorum longus muscle of the separated leg, and angles of metatarsophalangeal joint (MTP) and proximal interphalangeal joint (PIP) of the second toe before and after application of the load were measured. According to the following equation, difference in angle of refraction before and after application of the load was calculated. For comparison, measurement was conducted in the same manner also for the case of administering saline in place of the antiadhesive gel.

Difference in angle of refraction before and after application of load (°)=(Angle of MTP after application of load+Angle of PIP after application of load)−(Angle of MTP before application of load+Angle of PIP before application of load)  [Numerical Formula 1]

Figure 6:
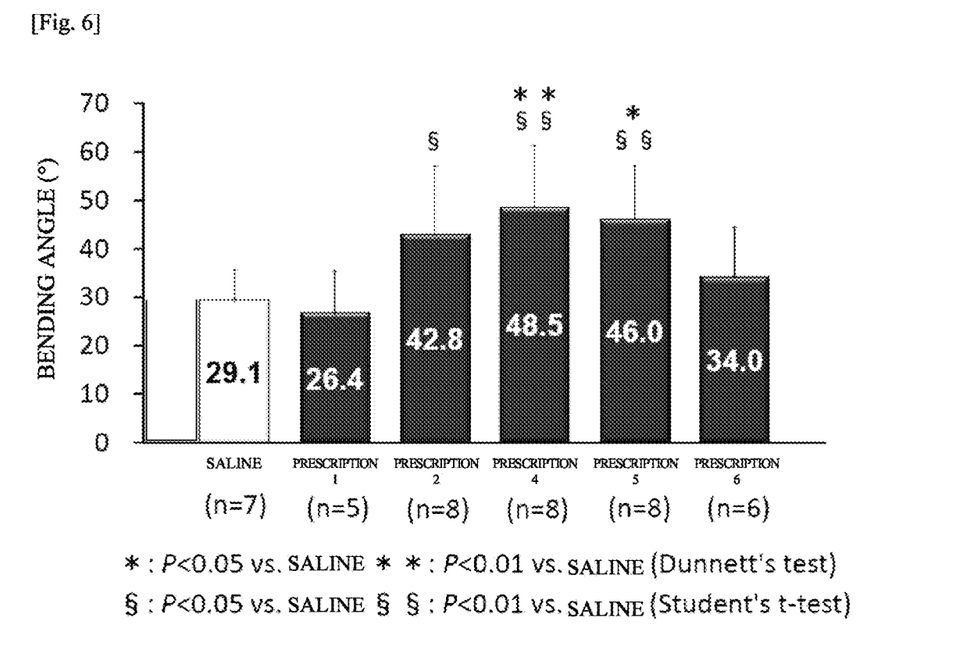
FIG. 6 is a chart illustrating measurement results of the range of motion of articulationes interphalangeae of an operated site (difference in angle of refraction before and after loading) of each group in Test Example 2.

The obtained result is shown in FIG. 6. From this result, it was confirmed that when the antiadhesive gel obtained from the antiadhesive material of the present invention is administered, the range of motion of the interphalangeal joint is extended, and adhesion after operation is effectively inhibited. Also, it was revealed that the antiadhesive gel obtained by mixing the antiadhesive material in purified water in a concentration of 5 to 15% by weight exerts an excellent antiadhesive effect.

Test Example 3. Peritoneum-Cecum Antiadhesive Effect

Using a male rat (Crlj: WI) (available from Charles River Laboratories Japan, Inc.), the effect of preventing adhesion between side-wall and cecum was evaluated. Concretely, first, a muscle piece of 1×4 cm of external oblique muscle of abdomen and internal oblique muscle of the abdomen of rat right peritoneum was excised, to prepare a side-wall. Then the interior of the side-wall was abraded with gauze. The cecum was extracted from the rat, and its entire area was abraded with gauze, and the cecum was then left still at room temperature for 20 minutes in the condition that it was exposed to the air. Then, the cecum was washed with saline (product of Otsuka Pharmaceutical factory, Inc.). Separately, the antiadhesive material having the composition shown in Table 1 was added to purified water so that the concentration was 15% by weight (Prescription 5) and shaken thoroughly, to prepare an antiadhesive gel, and the antiadhesive gel was administered to cover the entire area of the washed cecum in 1 minute after end of stirring. Then, the cecum treated as mentioned above was returned inside the abdominal cavity while it was brought into contact with the side-wall and the abdominal cavity was closed, and the rat was fed for one week. After one week, the abdominal cavity was opened, and the condition of adhesion between the side-wall and the cecum was observed. As to the condition of adhesion, an adhesion site score and an adhesion degree score were determined according to the criteria shown below, and a total of these scores was determined as a total adhesion score. In the present test, the test was conducted in the same manner for the case where saline was administered as a control in place of the antiadhesive gel.

<Adhesion Site Score>
Score: Condition
0: No adhesion
1: Adhesion observed only in side-wall separated site 2: Adhesion observed both in side-wall separated site and inside side-wall <Adhesion Degree Score>

Score: Condition

1: Slight adhesion; adhesion easily peelable with fingers

2: Moderate adhesion; adhesion requiring blunt peeling but peelable

3: Severe adhesion; adhesion requiring acute peeling, and unpeelable without tissue damage The obtained result is shown in Table 4. From this result, it was confirmed that the antiadhesive gel obtained by using the antiadhesive material exerts an excellent antiadhesive effect in the field of gastroenterology.

TABLE 4

| Group | Adhesion site score | Adhesion degree score | Total |
|---|---|---|---|
| Saline | 2 | 2 | 4 |
| (n = 6) | 2 | 2 | 4 |
| | 1 | 2 | 3 |
| | 1 | 2 | 3 |
| | 2 | 2 | 4 |
| | 2 | 2 | 4 |
| Prescription 5 | 1 | 3 | 4 |
| (n = 6) | 0 | 0 | 0 |
| | 0 | 0 | 0 |
| | 0 | 0 | 0 |
| | 0 | 0 | 0 |
| | 0 | 0 | 0 |

What is claimed is:

1. An adhesion prevention method, comprising the steps of: mixing a powdery antiadhesive material comprising alginic acid and/or a salt thereof with an aqueous solvent, selecting the mixture of the antiadhesive material and the aqueous solvent with the viscosity at 37° C. of less than or equal to 70 mPas·s at the time of 5 minutes after mixing with the aqueous solvent, and the viscosity at 37° C. of more than or equal to 120 mPas·s at the time of 60 minutes after mixing with the aqueous solvent, and applying the mixture to an affected tissue where prevention of adhesion is required within 5 minutes after the mixing step.

2. The adhesion prevention method according to claim 1, wherein the antiadhesive material further comprises a bivalent metal salt of an organic acid and/or an inorganic acid.

3. The adhesion prevention method according to claim 1, wherein the antiadhesive material further comprises a polyethylene glycol.

4. The adhesion prevention method according to claim 1, wherein the antiadhesive material further comprises an organic acid and/or an alkali metal salt thereof.

5. The adhesion prevention method according to claim 2, wherein the bivalent metal salt of an organic acid and/or an inorganic acid is a calcium salt of an organic acid and/or an inorganic acid.

6. The adhesion prevention method according to claim 4, wherein the organic acid and/or the alkali metal salt thereof is at least one selected from the group consisting of glucono-δ-lactone, gluconic acid, and an alkali metal salt of gluconic acid.

7. The adhesion prevention method according to claim 1, wherein the amount of the alginic acid and/or the salt thereof contained in the antiadhesive material is 1 to 4% by weight upon use.

* * * * *